(12) United States Patent
Ren et al.

(10) Patent No.: US 10,316,052 B2
(45) Date of Patent: Jun. 11, 2019

(54) FIDAXOMICIN PURIFICATION METHOD

(71) Applicant: ZHEJIANG HISUN PHARMACEUTICAL CO., LTD., Taizhou, Zhejiang (CN)

(72) Inventors: Huijun Ren, Shanghai (CN); Daochao Li, Shanghai (CN); Xuexiao Ying, Shanghai (CN); Feng Chen, Shanghai (CN); Linghui Zheng, Shanghai (CN); Lingping Wang, Shanghai (CN); Hua Bai, Shanghai (CN)

(73) Assignee: ZHEJIANG HISUN PHARMACEUTICAL CO., LTD., Taizhou, Zhejiang (CN)

( * ) Notice: Subject to any disclaimer, the term of this patent is extended or adjusted under 35 U.S.C. 154(b) by 106 days.

(21) Appl. No.: 15/324,555

(22) PCT Filed: Jul. 7, 2015

(86) PCT No.: PCT/CN2015/083435
§ 371 (c)(1),
(2) Date: Jan. 6, 2017

(87) PCT Pub. No.: WO2016/004848
PCT Pub. Date: Jan. 14, 2016

(65) Prior Publication Data
US 2018/0179244 A1  Jun. 28, 2018

(30) Foreign Application Priority Data
Jul. 9, 2014  (CN) .......................... 2014 1 0324018

(51) Int. Cl.
C07H 1/06   (2006.01)
C07H 17/08  (2006.01)
C12P 19/62  (2006.01)

(52) U.S. Cl.
CPC .............. *C07H 1/06* (2013.01); *C07H 17/08* (2013.01); *C12P 19/62* (2013.01)

(58) Field of Classification Search
CPC ....................................................... C07H 1/06
See application file for complete search history.

(56) References Cited

U.S. PATENT DOCUMENTS

| | | | |
|---|---|---|---|
| 7,378,508 B2 | 5/2008 | Chiu et al. | |
| 7,507,564 B2 | 3/2009 | Shue et al. | |
| 7,863,249 B2 | 1/2011 | Chiu et al. | |
| 8,859,510 B2 | 10/2014 | Chiu et al. | |
| 8,883,986 B2 | 11/2014 | Chiu et al. | |
| 2007/0259949 A1 | 11/2007 | Chiu et al. | |
| 2008/0194497 A1 | 8/2008 | Chiu et al. | |
| 2009/0163428 A1 | 6/2009 | Chiu et al. | |
| 2010/0081800 A1 | 4/2010 | Chiu et al. | |
| 2013/0252914 A1 | 9/2013 | Chiu et al. | |
| 2013/0331347 A1 | 12/2013 | Shue et al. | |
| 2016/0265071 A1 | 9/2016 | Xu et al. | |

FOREIGN PATENT DOCUMENTS

| | | |
|---|---|---|
| CN | 101663312 A | 3/2010 |
| CN | 102993251 A | 3/2013 |
| CN | 103275152 A | 9/2013 |
| CN | 103320355 A | 9/2013 |
| CN | 104098637 A | 10/2014 |
| CN | 104513286 A | 4/2015 |
| CN | 104560766 A | 4/2015 |
| EP | 2647643 A2 | 10/2013 |
| JP | S50111290 A | 9/1975 |
| JP | 2005534332 A | 11/2005 |
| JP | 2010516681 A | 5/2010 |
| WO | WO-2004014295 A2 | 2/2004 |
| WO | WO-2011146621 A2 | 11/2011 |
| WO | WO-2013170142 A1 | 11/2013 |
| WO | WO-2014023616 A1 | 2/2014 |
| WO | WO-2014174528 A2 | 10/2014 |
| WO | WO-2015055107 A1 | 4/2015 |

OTHER PUBLICATIONS

Kurabachew et al. J of Antimicrobial Chemotherapy, 2008, 62:713-719.*
Shahtalebi et al. Iran J Environ. Helath Sci Eng., 2011, 8(2):109-116.*
White et al. The J of Antibiotics, 1981, XXXIV(7):836-844.*
The Journal of Antibiotics, 1986 vol. XXXIX, No. 10, p. 1407-1412.
The First Office Action dated Apr. 3, 2018 issued on counterpart Japanese patent application 2017-500824.
International Search Report dated Jan. 4, 2018 in corresponding/related Application No. 15818964.7-1452.
Tu, Conghui et al., "Separation Mechanism of Nanofiltration Membrane and Its Application in Separation and Purification of Pharmaceutical Products", Proceedings of the Forth National Pharmaceutical Industry Symposium on Membrane Separation Technology Applications, 2007, pp. 138-149.
Notification of Reasons for Refusal issued in Japanese patent application No. 2017-500824 dated Jan. 8, 2019.

* cited by examiner

*Primary Examiner* — Bin Shen
(74) *Attorney, Agent, or Firm* — Harness, Dickey & Pierce, P.L.C.

(57) ABSTRACT

A fidaxomicin purification method, comprising: fermenting *Actinoplanes* sp. HS-16-20 to generate fermented liquid; conducting solid/liquid separation on the fermented liquid, soaking mycelium in an organic solvent, and filtering to obtain a solution containing fidaxomicin; treating the solution with nanofiltration concentrate, and separating to obtain fidaxomicin crude product; conducting preparative column chromatography on the fidaxomicin crude product, eluting with an acid aqueous solution containing an organic solvent, and separating to obtain the refined fidaxomicin product.

15 Claims, 2 Drawing Sheets

FIDAXOMICIN PURIFICATION METHOD

The present application claims priority of Chinese Patent Application CN201410324018.7 filed on Jul. 9, 2014, the contents of which are incorporated herein by reference in their entireties.

FIELD OF INVENTION

The present invention relates to pharmaceutical field, in particular relates to a purification method of antibiotic fidaxomicin.

PRIOR ARTS

Fidaxomicin is a novel macrolide antibacterial drug with a narrow spectrum developed by Op-timer Pharmaceutical Corporation in recent years and was licensed to sale in the market by FDA on May 27, 2011 in the United States under the trade name Dificid. The drug is mainly used for the treatment of *Clostridium difficile* associated diarrhea (CDAD).

The structural formula of fidaxomicin is shown as follows:

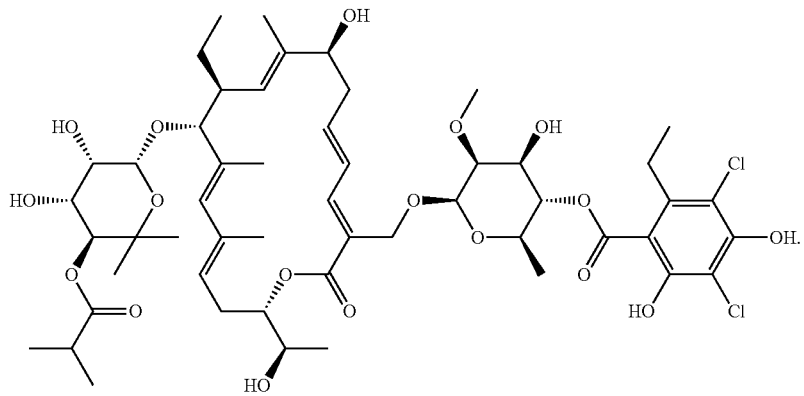 [SMILES: CCc1c(Cl)c(O)c(Cl)c(O)c1C(=O)O[C@H]1[C@H](O)[C@H](OC)[C@H](OC/C2=C\C=C\C[C@H](O)/C(C)=C/[C@H](CC)[C@@H](O[C@@H]3OC(C)(C)[C@@H](OC(=O)C(C)C)[C@H](O)[C@@H]3O)/C(C)=C/C(C)=C/C[C@@H]([C@@H](C)O)OC2=O)O[C@@H]1C]

Currently, the processes for separating and purifying fidaxomicin disclosed are mainly as follows:

CN103275152A has disclosed a process for preparing fidaxomicin with high purity. The process comprises filtering fidaxomicin fermentation broth to obtain mycelium, followed by soaking the mycelium in a polar solvent and conducting a solid/liquid separation to obtain fidaxomicin extraction, diluting the extraction with water followed by being introduced into and treated by macroporous decolorization resin to obtain a decolorized solution, introducing the decolorized solution into macroporous adsorption resin and gradient eluting with an analytical agent after saturated sorption, followed by concentrating, extracting, and drying to obtain fidaxomicin crude, dissolving the crude with a polar solvent followed by injecting into polymer microspheres for column chromatography, gradient eluting with an eluent, collecting the eluate, gathering the eluate where the content of fidaxomicin is more than 95% according to HPLC, concentrating and drying to obtain fidaxomicin with HLPC content of more than 97.1%.

CN101663312A has disclosed a process for preparing fidaxomicin. The process comprises adding an absorbent resin to the culture medium of fermentation broth, separating the solid substance (comprising the absorbent resin) from the fermentation broth after the fermentation is finished, eluting the solid substance with an organic solvent such as ethyl acetate, and then concentrating under reduced pressure to obtain a fidaxomicin crude. The purification is carried out by using a silica column containing Biotage KP-C18-HS, followed by concentrating, crystallizing and drying to obtain fidaxomicin with purity of 78%-94.7%.

CN102993251A has disclosed a process for purifying fidaxomicin by high performance liquid chromatography. The process comprises purifying a crude fidaxomicin with purity of 78% twice by Uni3OBPC to obtain fidaxomicin eluate with purity up to 98%.

WO2011146621A2 has disclosed a process for preparing fidaxomicin comprising preparing fidaxomicin with purity around 93% by liquid phase.

The purity of fidaxomicin prepared by above mentioned processes is no more than 99%, which still cannot meet the requirements of pharmaceutical production. Thus, a process for preparing fidaxomicin with high purity is urgently desired to meet the requirements of pharmaceutical production.

CONTENTS OF THE PRESENT INVENTION

The purpose of the present invention is to provide an environmental friendly and simplified process for purifying fidaxomicin, which can be arrived at by the following technical solution:

a fidaxomicin purification process, comprising:

(1) conducting preparative column chromatography on a crude fidaxomicin, eluting with an acid aqueous solution containing an organic solvent, collecting and combining the eluate containing fidaxomicin; and (2) separating the eluate obtained according to step (1) to give the refined fidaxomicin.

Wherein, the preparative column used in step (1) can be a common preparative column in the art, generally is a reversed-phase column. In the present invention, DAC200 preparation column (200×250 mm) supplied by Beijing Chuangxin Tong Heng Science &Technology Co., Ltd. is preferred. The filler for the preparative column can be common filler used in the art, preferably C8 filler. C8 filler refers to octylsilane bonded silica gel, which is generally commercially available in the art, whose particle size is typically 10 μm, can be selected from HuaPu C8 filler, nanomicro C8 filler, Agela C8 filler or kromasil C8 filler, preferably kromasil C8 filler.

Wherein, the organic solvent used in step (1) can be a common organic solvent in the art, preferably methanol or acetonitrile; the acid aqueous solution is an aqueous solution of formic acid. Preferably, the acid aqueous solution containing an organic solvent used in step (1) is a solution formed by methanol:water:formic acid=(55-75):(45-25):0.1 (V:V:V), or acetonitrile:water:formic acid=(45-65):(55-35):0.1 (V:V:V), more preferably a solution formed by methanol:water:formic acid=(60-70):(40-30):0.1 (V:V:V), or acetonitrile:water:formic acid=(50-60):(50-40):0.1 (V:V:V), most preferably a solution formed by methanol:water:formic acid=65:35:0.1 (V:V:V), or acetonitrile:water:formic acid=55:45:0.1 (V:V:V). The above mentioned V:V:V refers to a volume ratio.

In the process of conducting the preparative column chromatography, other chromatographic conditions can be common chromatographic conditions used in the art. In the present invention, the following chromatographic conditions are preferred. The high performance liquid chromatograph can be a common chromatograph in the art, preferably LC2010HT high-performance liquid chromatography supplied by Shimadzu. The column temperature can be common column temperature used in the art, preferably 20-30° C. The detection wavelength is generally 250 nm. The flow rate is generally 1.0 mL/min. The injection volume is generally 10 µL.

Wherein, in step (1), collecting and combining the eluate containing fidaxomicin with HPLC purity ≥99.5%.

Wherein, the crude fidaxomicin used in step (1) can be prepared according to a common preparation process in the art. Generally, it is required that the HPLC purity of crude fidaxomicin is no less than 70%, for example, 72.6%, 70.9%, 72% or 73.5%. In the present invention, the crude fidaxomicin is prepared according to the following process:

(a) pre-treating fidaxomicin fermentation broth to obtain a solution containing fidaxomicin;

(b) conducting nanofiltration and concentrating on the solution containing fidaxomicin obtained according to step (a) to give a concentrated solution containing fidaxomicin;

(c) separating the concentrated solution containing fidaxomicin obtained according to step (b) to give the crude fidaxomicin.

Wherein, in step (a), the fidaxomicin fermentation broth can be prepared according to a common preparation process in the art. Preferably, the present invention comprises:

① incubating a producer strain of fidaxomicin into a plate medium, culturing to make mycelium matured, thereby obtaining a colony of producing fidaxomicin;

② incubating the colony of producing fidaxomicin obtained according to step ① into a shaking flask of seed medium, culturing, thereby obtaining a seed culture;

③ incubating the seed culture obtained according to step ② into a seed tank medium, culturing, thereby obtaining a seed culture of fermenter;

④ incubating the seed culture of fermenter obtained according to step ③ into a fermentation medium, culturing, thereby obtaining fidaxomicin fermentation broth.

The producer strain of fidaxomicin in step ① generally refers to the strain that produces fidaxomicin after fermentation incubation. In the present invention, *Actinoplanes* sp. HS-16-20 is preferred, which has been preserved in China General Microbiological Culture Collection Center on Mar. 11, 2013, whose address is Institute of Microbiology Chinese Academy of Sciences, Yard 1, West Beichen Road, Chaoyang District, Beijing. Accession number is CGMCC No. 7294, classified as *Actinoplanes* sp., registered and proven to survive. The plate medium can be a common plate medium used in the art, preferably ISP2 medium. The ISP2 medium preferably includes glucose 4 g, yeast extract 4 g, malt extract 10 g, agar 15 g and water for the rest in every 1 L medium. The pH value of ISP2 medium is preferably 7.3. The plate medium generally undergoes sterilization before use. The process of sterilization can be a common process used in the art. The pressure used for sterilization is preferably 1.05 kg/cm$^2$. The period for sterilization is preferably 20 min. The temperature for incubation can be common temperature used in the art, preferably 27-29° C., more preferably 28° C. The period for incubation can be common in the art, as long as ensuring that the strain mycelium which produces fidaxomicin are matured, preferably 8 days.

In step ②, the shaking flask seed medium can be a common shaking flask seed medium in the art, preferably comprising sucrose 2 g, sorbitol 3 g, cottonseed meal 3 g, peanut meal 1.5 g, CaCO$_3$ 0.6 g, MgSO$_4$.7H$_2$O 0.3 g and water for the rest in every 1 L seed medium. The pH value of the shaking flask seed medium is preferably 7.2. The shaking flask seed medium generally undergoes sterilization before use. The process of sterilization can be a common process in the art. The temperature for sterilization is preferably 121° C. The period for sterilization is preferably 30 min. The inoculum rate for shaking flask seed medium is common in the art, preferably 10$^5$-10$^6$ c.f.u per milliliter (mL) of seed culture. The temperature for incubation can be common temperature used in the art, preferably 27-29° C., more preferably 28° C. The manner for incubation can be a common manner in the art, preferably shaking bed incubation. The rotational speed of cultivation is preferably 250 rpm. The period for cultivation can be common in the art, preferably 28 hours. After incubation, the pH value of seed culture is generally between 6.8 and 7.0. The concentration of the strain mycelium which produces fidaxomicin in the shaking flask seed liquid is generally 25%-30%, the percentage refers to the volume of the strain mycelium which produces fidaxomicin accounting for the volume of the shaking flask seed liquid.

In step ③, the seed tank medium can be a common seed tank medium in the art, preferably comprising sucrose 10 g, sorbitol 2 g, soluble starch 3 g, (NH$_4$)$_2$SO$_4$ 0.5 g, beef extract 2 g, peanut meal 1 g, KH$_2$PO$_4$ 0.04 g and water for the rest in every 1 L seed tank medium. The seed tank medium generally undergoes sterilization before use. The process for sterilization can be a common process in the art, preferably steam sterilization. The temperature for steam sterilization can be common temperature used in the art, preferably 121° C. The period for steam sterilization can be common in the art, preferably 30 min. The inoculum rate for seed tank medium is common in the art. The ratio of seed culture volume in shaking flask to seed medium volume in seed tank is 0.01:1. The temperature for incubation can be common temperature used in the art, preferably 27-29° C., more preferably 28° C. The manner of incubation can be a common manner in the art. The rotational speed of incubation is preferably 200 rpm. The ventilation (air) volume during the period of incubation is preferably 1 vvm. The period for incubation can be common in the art, preferably 24 hours. After incubation, the pH value of seed culture in seed tank is generally between 6.8 and 7.0. The concentration of the strain mycelium which produces fidaxomicin in the seed tank culture liquid is generally between 25% and 30%, the percentage refers to the volume of the strain mycelium which produces fidaxomicin accounting for the volume of the seed tank culture liquid.

In step ④, the fermentation medium can be a common fermentation medium in the art, preferably comprising sucrose 10 g, sorbitol 2 g, soluble starch 3 g, $(NH_4)_2SO_4$ 0.5 g, beef extract 2 g, peanut meal 1 g, $KH_2PO_4$ 0.04 g and water for the rest in every 1 L fermentation medium. The fermentation medium may further comprise a defoamer, the defoamer can be a common defoamer in the art, preferably PPG. The dosage of the defoamer can be a common dosage in the art, preferably 1% of the mass of the fermentation medium. The fermentation medium generally undergoes sterilization before use. The process for sterilization can be a common process in the art, preferably steam sterilization. The temperature for steam sterilization can be common temperature used in the art, preferably 121° C. The period for steam sterilization can be common in the art, preferably 20 min. The temperature for incubation can be common temperature used in the art, preferably 27-29° C., more preferably 28° C. The manner for incubation can be a common manner in the art. The rotational speed for incubation is preferably 200 rpm-300 rpm. The ventilation volume during the period of incubation is preferably 0.8-1.0 vvm. The period for incubation can be common in the art, preferably 8 hours.

The titer of fidaxomicin is generally no less than 2000 mg/L with the above preparation process, preferably between 2800 mg/L and 3200 mg/L.

The present invention also provides fidaxomicin fermentation broth, which is prepared by incubating the producer strain of fidaxomicin. The titre of fidaxomicin is no less than 2000 mg/L in the fermentation broth, preferably between 2800 mg/L and 3200 mg/L. The producer strain of fidaxomicin is preferably *Actinoplanes* sp. HS-16-20, accession number is CGMCC No. 7294.

Wherein, the pre-treating in step (a) comprises conducting solid/liquid separation on fidaxomicin fermentation broth to obtain mycelium, followed by soaking the mycelium in an organic solvent which is preferably a common organic solvent used for soaking strain mycelium which produces fidaxomicin in the art, more preferably methanol or ethanol, most preferably ethanol, and then filtering to obtain a solution containing fidaxomicin. The dosage of the organic solvent can be commonly used in the art, preferably, the ratio of the volume of the organic solvent to the mass of the mycelium is 2.5-3.5 L/kg, more preferably 2.9-3.0 L/kg (for example 22 L/7.4 kg, 21 L/7.1 kg, 24 L/8.4 kg, 23 L/7.8 kg).

Wherein, the nanofiltration membrane used for the nanofiltration and concentrating in step (b) can be a common nanofiltration membrane in the art, preferably DK or DL nanofiltration membrane, more preferably DL nanofiltration membrane. Preferably, in the concentrated solution obtained by nanofiltration and concentrating, the unit of fidaxomicin is ≥10000 mg/L.

Wherein, the crude fidaxomicin can be separated from the concentrated solution obtained according to step (b) by employing a known process in the art. In a specific embodiment, an anti-solvent, preferably water, can be added. After the concentrated solution going through nanofiltration membrane was added with water, the volume concentration of the organic solvent in the concentrated solution (the concentrated solution obtained after the addition of water) is less than 35%, preferably 25%-30%, the percentage refers to the volume of the organic solvent accounting for the total volume of the concentrated solution obtained after the addition of water.

Wherein, the refined fidaxomicin can be separated from the eluate obtained according to step (1) by employing a known process in the art. In a specific embodiment, an anti-solvent, preferably water, can be added and the ratio of the addition amount of water to the volume of the eluate collected in step (1) is (1-2):1, preferably (1.4-1.6):1.

The advantages of the present inventions are:
the present invention uses nanofiltration membrane to concentrate the pre-treated fidaxomicin fermentation broth in the process for preparing the crude fidaxomicin, thereby removing most of the inorganic salts and pigment substances in the fermentation broth; and finally chooses C8 filler for the preparative column to make the impurities and fidaxomicin separated effectively, which leads to the resultant fidaxomicin with HPLC purity ≥99.5% and yield ≥50%. Moreover, the organic solvent used in the present invention can be recycled, discharge of the three wastes is low and it is environmental friendly, meets the trends and requirements of the current pharmaceutical production well.

Information of Biomaterials

The *Actinoplanes* sp. HS-16-20 strain used in the present invention has been deposited in China General Microbiological Culture Collection Center (CGMCC) on Mar. 11, 2013, whose address is Institute of Microbiology Chinese Academy of Sciences, Yard 1, West Beichen Road, Chaoyang District, Beijing, postal code is 100101, accession number is CGMCC No. 7294, classified as *Actinoplanes* sp., registered and proven to survive.

DETAILED DESCRIPTION OF THE PREFERRED EMBODIMENT

Figure 1:
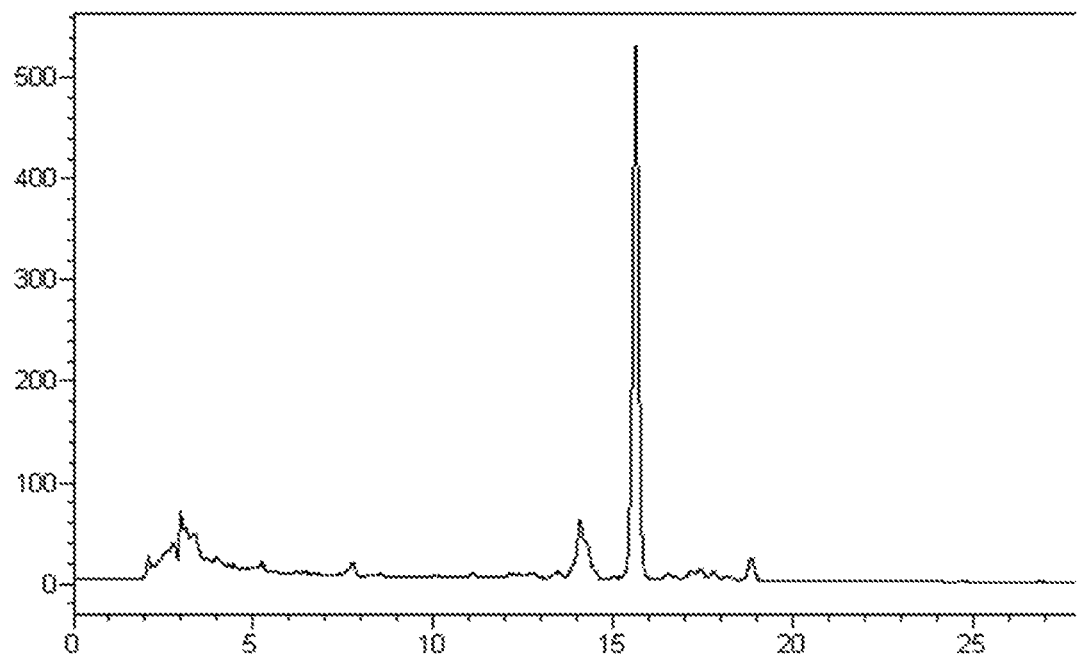
FIG. 1 is HPLC graph of the fidaxomicin fermentation broth in embodiment 1.

The *Actinoplanes* sp. used for fermentation culture in the present invention has been deposited in China General Microbiological Culture Collection Center on Mar. 11, 2013, whose accession number is CGMCC No. 7294; more details is recited in Chinese patent application CN201310501389.3 filed on Oct. 16, 2013, the contents of which are incorporated herein by reference in their entireties. The nanofiltration membrane is supplied by General Electric Company (GE); the preparation column is supplied by Beijing Tong Heng Innovation Technology Co., Ltd.; the C8 filler is supplied by Acchorom Technology and Akzo Nobel Company; the high performance liquid chromatograph is LC2010HT supplied by Shimadzu; the ethanol and methanol added into the fidaxomicin mycelium are commercially available industrial grade; the methanol and acetonitrile used for preparation are commercially available chromatographic grade; the formic acid is commercially available reagent grade. The chromatographic purity in the following embodiments refers to HPLC purity, and ventilation means introducing the air.

The process for incubating the fermentation broth of the present invention is as below:

(1) Preparing and Incubating Plate Colony

ISP2 medium was employed as the plate medium, the formulation of ISP2 medium comprised (g/L): glucose 4, yeast extract 4, malt extract 10, agar 15, and distilled water was added to reach a constant volume of 1000 mL, pH 7.3, wherein g/L referred to the mass of each component in 1 L ISP2 medium. The ISP2 medium underwent sterilization for 20 min at a pressure of 1.05 kg/cm² before use, and then was poured into the plate after cooled to 50-60° C., *Actinoplanes* sp. (CGMCC No. 7294) mycelium was inoculated, incubated at 28±1° C. for 8 days, the mycelium was mature, and a *Actinoplanes* sp. colony was obtained.

(2) Preparing and Incubating the Shaking Flask Seed Liquid

The formulation of the seed medium included (g/L): sucrose 2, sorbitol 3, cottonseed meal 3, peanut meal 1.5, CaCO₃ 0.6, MgSO₄.7H₂O 0.3 and water was added to reach a constant volume of 1000 mL, pH 7.2, wherein g/L referred to the mass of each component in 1 L seed medium. The liquid volume for the shaking flask was 25 mL/250 mL, i.e. 25 mL seed medium in 250 mL shaking flask. The seed medium underwent sterilization at 121° C. for 30 min before use. Then the *Actinoplanes* sp. colony obtained according to step (1) was inoculated into the seed medium with a inoculum rate of 10⁵-10⁶ c.f.u/mL, incubated in a shaking bed at 28±1° C. and 250 rpm for 28 hours, pH value of the culture liquid usually 6.8-7.0, the (*Actinoplanes* sp.) mycelium concentration was 25-30% (volume percent).

(3) Preparing the Seed Tank Culture Liquid

10 L seed medium was inoculated into a 15 L seed tank (the formulation of the seed tank medium included (g/L): sucrose 10, sorbitol 2, soluble starch 3, (NH₄)₂SO₄ 0.5, beef extract 2, peanut meal 1, KH₂PO₄ 0.04, and water was added to reach a constant volume of 1000 mL, wherein g/L referred to the mass of each component in 1 L seed tank medium), and steam sterilization was conducted at 121° C. for 30 min. After cooling, 100 mL shaking flask seed liquid was inoculated into the seed tank, incubated at 28±1° C. under a rotational speed of 200 rpm and 1 vvm (ventilation volume) for 24 hours, pH value of the culture liquid usually 6.8-7.0, the (*Actinoplanes* sp.) mycelium concentration was 25-30% (v/v).

(4) Preparing and Incubating the Fermentation Tank Medium

The formulation of the fermentation medium included (g/L): sucrose 10, sorbitol 2, soluble starch 3, (NH₄)₂SO₄ 0.5, beef extract 2, peanut meal 1, KH₂PO₄ 0.04 and water was added to reach a constant volume of 1000 mL, wherein g/L referred to the mass of each component in 1 L fermentation medium. 1% PPG (polypropylene glycol) was added into the fermentation medium as a defoamer. The feeding volume was 35 L (i.e. 35 L fermentation medium), pH was at 7.0, and steam sterilization was conducted at 121° C. for 20 min. After cooling, about 3.5 L seed tank culture liquid was inoculated, incubated at 28±1° C. under a rotational speed of 200-300 rpm and 0.8-1.0 vvm (ventilation volume) for 8 days.

Embodiment 1

Figure 2:
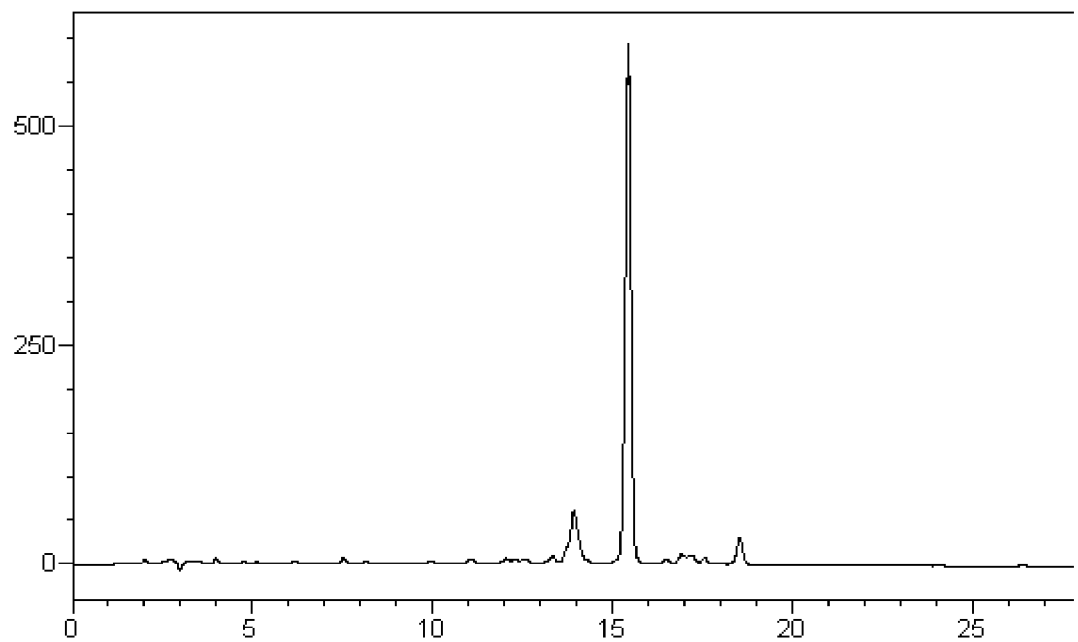
FIG. 2 is HPLC graph of the precipitated crude fidaxomicin prepared according to embodiment 1.

30 L fermentation broth containing a fidaxomicin fermenting unit of 3026 mg/L (liquid chromatogram referring to FIG. 1) was filtered to obtain 7.4 kg mycelium, and the mycelium was soaked in 22 L ethanol and then filtered, the soaked filtrate was collected, nanofiltrated and concentrated via a DK nanofiltration membrane until fidaxomicin unit was more than 10000 mg/L, followed by adding purified water to the concentrated solution until the ethanol concentration reached 30%, continuing stirring for 30 min and filtering to give a crude fidaxomicin (liquid chromatogram referring to FIG. 2) with chromatographic purity of 72.6%.

Figure 3:
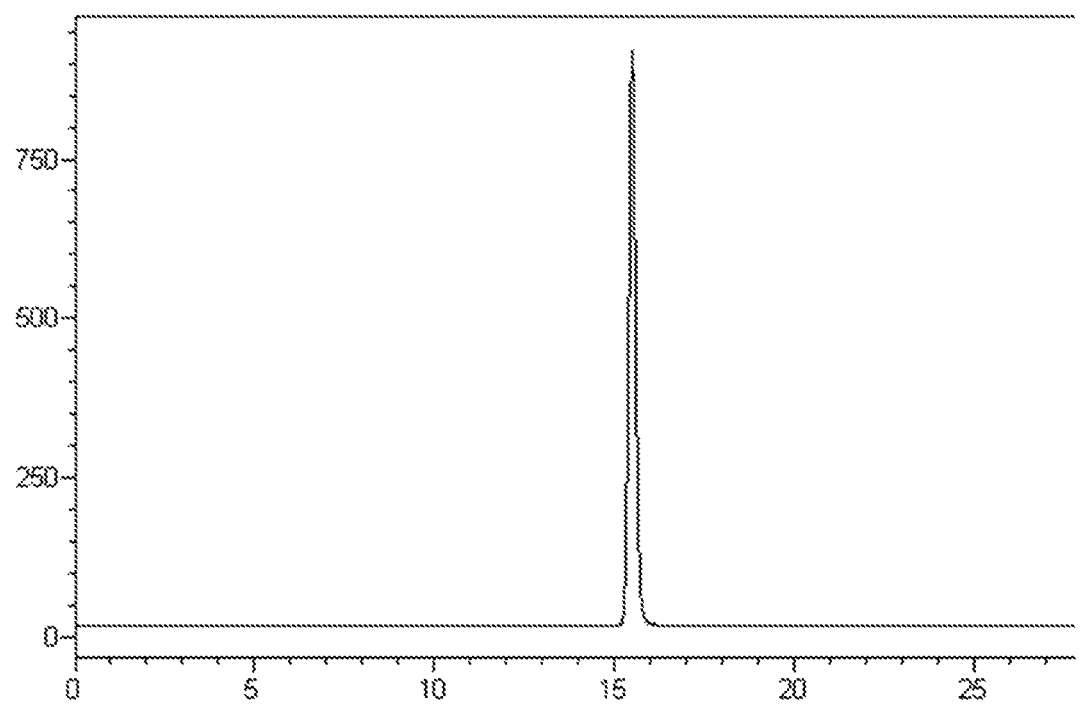
FIG. 3 is HPLC graph of the refined fidaxomicin prepared according to embodiment 1.

The crude fidaxomicin was purified by DAC200 preparation column packed with C8 filler (supplied by HuaPu) and mobile phase was acetonitrile:water:formic acid=55:45:0.1 (v:v:v), fractions of HPLC purity≥99.5% were collected and combined, 1.5 times volume of purified water was added under stirring, filtered and dried to give 47.7 g fidaxomicin dry powder with chromatographic purity of 99.67% (liquid chromatogram referring to FIG. 3) and the total extraction yield was 52.5%.

Embodiment 2

30 L fermentation broth containing fidaxomicin fermenting unit of 2963 mg/L was filtered to obtain 7.1 kg mycelium, and the mycelium was soaked in 21 L methanol and then filtered, the soaked filtrate was collected, nanofiltrated and concentrated via a DK nanofiltration membrane until fidaxomicin unit was more than 10000 mg/L, followed by adding purified water to the concentrated solution until the methanol concentration reached 30%, continuing stirring for 30 min and filtering to give a crude fidaxomicin with chromatographic purity of 70.9%.

The crude fidaxomicin was purified by DAC200 preparation column packed with C8 filler (supplied by HuaPu) and mobile phase was methanol:water:formic acid=65:35:0.1 (v:v:v), fractions of HPLC purity≥99.5% were collected and combined, 1.5 times volume of purified water was added under stirring, filtered and dried to give 45.6 g fidaxomicin dry powder with chromatographic purity of 99.58% and the total extraction yield was 51.3%.

Embodiment 3

30 L fermentation broth containing fidaxomicin fermenting unit of 3079 mg/L was filtered to obtain 8.1 kg mycelium, and the mycelium was soaked in 24 L ethanol and then filtered, the soaked filtrate was collected, nanofiltrated and concentrated via a DL nanofiltration membrane until fidaxomicin unit was more than 10000 mg/L, followed by adding purified water to the concentrated solution until the ethanol concentration reached 30%, continuing stirring for 30 min and filtering to give a crude fidaxomicin with chromatographic purity of 72.0%.

The crude fidaxomicin was purified by DAC200 preparation column packed with kromasil C8 filler and mobile phase was acetonitrile:water:formic acid=55:45:0.1 (v:v:v), fractions of HPLC purity≥99.5% were collected and combined, 1.5 times volume of purified water was added under stirring, filtered and dried to give 48.1 g fidaxomicin dry powder with chromatographic purity of 99.62% and the total extraction yield was 52.1%.

Embodiment 4

30 L fermentation broth containing a fidaxomicin fermenting unit of 3102 mg/L was filtered to obtain 7.8 kg mycelium, and the mycelium was soaked in 23 L ethanol and then filtered, the soaked filtrate was collected, nanofiltrated and concentrated via a DL nanofiltration membrane until fidaxomicin unit was more than 10000 mg/L, followed by adding purified water to the concentrated solution until the ethanol concentration reached 30%, continuing stirring for 30 min and filtering to give a crude fidaxomicin with chromatographic purity of 73.5%.

The crude fidaxomicin was purified by DAC200 preparation column packed with kromasil C8 filler and mobile phase was methanol:water:formic acid=65:35:0.1 (v:v:v), fractions of HPLC purity≥99.5% were collected and combined, 1.5 times volume of purified water was added under stirring, filtered and dried to give 49.0 g fidaxomicin dry powder with chromatographic purity of 99.68% and the total extraction yield was 52.7%.

It is to be understood that the foregoing description of the preferred embodiments is intended to be purely illustrative of the principles of the invention, rather than exhaustive thereof, and that changes and variations will be apparent to those skilled in the art, and that the present invention is not intended to be limited other than expressly set forth in the following claims.

What is claimed is:

1. A fidaxomicin purification process, comprising:
   (1) conducting preparative column chromatography with a preparative column on a crude sample comprising fidaxomicin, eluting the fidaxomicin from the crude sample with an acid aqueous solution containing an organic solvent to generate eluates containing the fidaxomicin, and collecting and combining the eluates containing the fidaxomicin to form an eluate containing the fidaxomicin; and
   (2) separating the fidaxomicin from the acid aqueous solution of the eluate to yield refined fidaxomicin;
   wherein the fidaxomicin is generated by *Actinoplanes* sp. HS-16-20, accession number is CGMCC No. 7294, and the acid aqueous solution containing an organic solvent is a solution comprising a methanol:water:formic acid ratio of 55-75:45-25:0.1, or an acetonitrile:water:formic acid ratio of 45-65:55-35:0.1 (v:v:v).

2. The process according to claim 1, wherein the crude sample comprising fidaxomicin in step (1) is prepared according to the following process:
   (a) pre-treating fidaxomicin fermentation broth to obtain a solution containing fidaxomicin;
   (b) conducting nanofiltration and concentrating on the solution containing fidaxomicin to generate a concentrated solution containing the fidaxomicin; and
   (c) separating the concentrated solution to yield the crude sample comprising fidaxomicin.

3. The process according to claim 2, wherein the pre-treating in step (a) comprises conducting a solid/liquid separation on the fidaxomicin fermentation broth to obtain mycelium, soaking the mycelium in an organic solvent, and filtering to obtain a solution containing fidaxomicin.

4. The process according to claim 3, wherein the organic solvent is methanol or ethanol.

5. The process according to claim 2, wherein the process for preparing fidaxomicin fermentation broth in step (a) comprises:
   ① incubating a producer strain of fidaxomicin in plate medium, culturing the producer strain to make mature mycelium, and obtaining a colony that produces fidaxomicin;
   ② incubating the colony in a shaking flask of seed medium, culturing the seed medium, and obtaining a seed culture;
   ③ incubating the seed culture in seed tank medium, culturing the seed tank medium, and obtaining a seed culture of fermenter; and
   ④ incubating the seed culture of fermenter in fermentation medium, culturing the fermentation medium, and obtaining the fidaxomicin fermentation broth.

6. The process according to claim 2, wherein the conducting nanofiltration and concentrating is performed with a DK or a DL nanofiltration membrane.

7. The process according to claim 2, wherein the concentrated solution containing the fidaxomicin has a fidaxomicin concentration of ≥10000 mg/L.

8. The process according to claim 2, wherein the separating of step (c) comprises adding an anti-solvent to the concentrated solution containing the fidaxomicin and separating the fidaxomicin from the anti-solvent to yield the crude sample comprising fidaxomicin.

9. The process according to claim 8, wherein the anti-solvent is water, and the addition of the water makes the concentration of the organic solvent in the concentrated solution less than 35%, wherein the percentage refers to the volume of the organic solvent in the concentrated solution accounting for the total volume of the concentrated solution obtained after the addition of the water.

10. The process according to claim 1, wherein the preparative column in step (1) contains C8 filler.

11. The process according to claim 1, wherein the acid aqueous solution containing the organic solvent used in step (1) is a solution comprising a methanol:water:formic acid ration of 60-70:40-30:0.1, or an acetonitrile:water:formic acid ratio of 50-60:50-40:0.1 (v:v:v).

12. The process according to claim 1, wherein the eluate containing the fidaxomicin has a purity of ≥99.5% as determined by high-performance liquid chromatography (HPLC).

13. The process according to claim 1, wherein separating comprises adding an anti-solvent into the eluate containing the fidaxomicin, and separating the refined fidaxomicin from the eluate.

14. The process according to claim 13, wherein the anti-solvent is water and the water is added to generate a water:eluate ratio of 1-2:1 (v:v).

15. A fidaxomicin purification process, comprising:
   incubating a producer strain of fidaxomicin in plate medium, culturing the producer strain to make mature mycelium, and obtaining a colony that produces fidaxomicin;
   incubating the colony in a shaking flask of seed medium, culturing the seed medium, and obtaining a seed culture;
   incubating the seed culture in seed tank medium, culturing the seed tank medium, and obtaining a seed culture of fermenter;
   incubating the seed culture of fermenter in fermentation medium, culturing the fermentation medium, and obtaining a crude sample comprising fidaxomicin;
   conducting preparative column chromatography with a preparative column on the crude sample comprising fidaxomicin, eluting the fidaxomicin from the crude sample with an acid aqueous solution containing an organic solvent to generate eluates containing the fidaxomicin, and collecting and combining the eluates containing the fidaxomicin to form an eluate containing the fidaxomicin; and
   separating the fidaxomicin from the acid aqueous solution of the eluate to yield refined fidaxomicin;
   wherein the fidaxomicin is generated by *Actinoplanes* sp. HS-16-20, accession number is CGMCC No. 7294, and the acid aqueous solution containing an organic solvent is a solution comprising a methanol:water:formic acid ratio of 55-75:45-25:0.1, or an acetonitrile:water:formic acid ratio of 45-65:55-35:0.1 (v:v:v).

* * * * *